United States Patent [19]

Bary

[11] Patent Number: 5,809,573
[45] Date of Patent: Sep. 22, 1998

[54] EXOTHERMIC CHEMICALLY HEATED EAR WARMER

[76] Inventor: Susan Bary, 109 Tilton Landing, Baytown, Tex. 77520

[21] Appl. No.: 581,969

[22] Filed: Jan. 2, 1996

[51] Int. Cl.$^6$ ...................................... A61F 11/14
[52] U.S. Cl. .............................. 2/209; 2/171.2; 128/866; 607/109
[58] Field of Search ........................... 2/171.2, 209, 423; 128/864, 866; 607/109

[56] References Cited

U.S. PATENT DOCUMENTS

| | | | |
|---|---|---|---|
| 2,149,383 | 3/1939 | Bean | 2/209 |
| 3,796,855 | 3/1974 | Brown et al. | 2/209 |
| 5,395,400 | 3/1995 | Stafford et al. | 2/209 |

*Primary Examiner*—Diana Biefeld
*Attorney, Agent, or Firm*—Kenneth A. Roddy

[57] ABSTRACT

An article of headgear has a headband portion and ear covering portions which cover the ears of the wearer and pair of open ended pockets in the ear covering portions which removably receive and carry a packet of exothermic heat dispensing material to warm the ears of the wearer. In a first embodiment, the headband is formed of a pair of curved bands of resilient flexible material curved to fit over the top of the person's head and slidably connected in overlapped relation such that the length of the headband portion may be adjusted to fit various head sizes, and the ear covering portions are ear pads secured on the outer ends of the headband. In a second embodiment, the headband is a continuous circular configuration formed of flexible elastic material which encircle the person's head and the laterally opposed ear covering portions and pockets are integrally formed on the circular headband. In a third embodiment the article is in the form of a cap having a crown portion which covers the top of the head of the wearer above the ears and is hemmed at its bottom end to form a circular headband portion which covers the ears of the wearer. The packets of exothermic heat dispensing material are activated by exposing them to air, kneading them, or puncturing an inner bag to initiate the heat generating chemical reaction prior to placing them into the pockets.

10 Claims, 5 Drawing Sheets

EXOTHERMIC CHEMICALLY HEATED EAR WARMER

BACKGROUND OF THE INVENTION

1. Field of the Invention

This invention relates generally to devices for warming the ears, and more particularly to such a device which is worn on the head and covers the ears of the wearer and removably receives and carries a pair of chemical exothermic heat dispersing packets.

2. Brief Description of the Prior Art

Ear warming devices are known in the art. There are several patents which disclose various ear warming devices.

Brown et al, U.S. Pat. No. 3,796,855 discloses an ear heating pad assembly comprising a pair of cup-shaped housings supported at the ends of a head band, each of which contains a heating coil and switch which are connected by electric cable to either a household electrical outlet or a dry cell battery.

Ellis, U.S. Pat. No. 4,034,787 discloses a hot water bottle having conical projections which is used to warm the outer ear cavity and ease the pain of earaches.

Clark, U.S. Pat. No. 5,009,228 discloses a rigid oval cup-shaped device for relieving ear pain comprised of a thermally conductive polymeric material having an interior which fits over a user's ear, and a hollow chamber which receives a heat source. In a preferred embodiment, the hollow chamber is filled with a liquid heat source such as water or a filler material saturated with water, and may be placed in a microwave oven or boiling water. Another embodiment has a heat dispersing medium permanently contained in the chamber and an integral electrical battery power source and metal heating coil for activating the heat dispersing medium.

U.S. Pat. Nos. 4,850,055 issued to Hwang and 4,935,965 issued to Wassell disclose ear muffs which do not contain a heat generating element.

Various types of exothermic heat dispensing packets known as hand warmers or hot packs are known in the art. The activation of these packets is accomplished by various means such as exposure to air, mixing with water, kneading, or puncturing of an inner bag to mix the chemicals and start the heat generating reaction.

U.S. Pat. No. 3,976,049, incorporated herein by reference, discloses an air activated exothermic hand warmer packet marketed by "Grabber" (tm) of concord, CA under the tradename "Grabber Mycoal". This patent is directed toward the unified structure of a warmer and air tight envelope. The warmer utilizes a mixture of iron powder, water, cellulose, vermiculite activated carbon, and salt, enclosed in a laminated bag having an air permeable cloth layer and an impermeable film layer containing aeration holes.

The present invention is distinguished over the prior art in general, and these patents in particular by an article of headgear having a headband portion and ear covering portions which cover the ears of the wearer and pair of open ended pockets in the ear covering portions which removably receive and carry a packet of exothermic heat dispensing material to warm the ears of the wearer. In a first embodiment, the headband is formed of a pair of curved bands of resilient flexible material curved to fit over the top of the person's head and slidably connected in overlapped relation such that the length of the headband portion may be adjusted to fit various head sizes, and the ear covering portions are ear pads secured on the outer ends of the headband. In a second embodiment, the headband is a continuous circular configuration formed of flexible elastic material which encircle the person's head and the laterally opposed ear covering portions and pockets are integrally formed on the circular headband. In a third embodiment the article is in the form of a cap having a crown portion which covers the top of the head of the wearer above the ears and is hemmed at its bottom end to form a circular headband portion which covers the ears of the wearer. The packets of exothermic heat dispensing material are activated by exposing them to air, kneading them, or puncturing an inner bag to initiate the heat generating chemical reaction prior to placing them into the pockets.

SUMMARY OF THE INVENTION

It is therefore an object of the present invention to provide an ear warming device which will warm the ears of the wearer to protect against cold weather or to soothe an earache.

It is another object of this invention to provide an ear warming headgear article which is comfortably supported on a person's head by a headband and has ear covering portions which substantially cover the ears of the wearer.

Another object of this invention to provide a headgear article which covers the head of a person and has pockets in an ear covering portion which receives an exothermic heat dispersing device to warm the ears of the wearer.

Another object of this invention is to provide an ear warming device which utilizes an exothermic heat dispersing medium to warm the ears of the wearer without overheating.

Another object of this invention is to provide an ear warming headgear article which will receive and carry various commercially available exothermic heat dispersing packets.

Another object of this invention is to provide an ear warming device which does not contain any electrical circuitry and does not require batteries, or connection to electrical outlets.

A further object of this invention is to provide an ear warming headgear article which is attractive in appearance.

A still further object of this invention is to provide an exothermic ear warming device which is simple in construction, economical to manufacture, and is safe and reliable in operation.

Other objects of the invention will become apparent from time to time throughout the specification and claims as hereinafter related.

The above noted objects and other objects of the invention are accomplished by an article of headgear having a headband portion and ear covering portions which cover the ears of the wearer and pair of open ended pockets in the ear covering portions which removably receive and carry a packet of exothermic heat dispensing material to warm the ears of the wearer. In a first embodiment, the headband is formed of a pair of curved bands of resilient flexible material curved to fit over the top of the person's head and slidably connected in overlapped relation such that the length of the headband portion may be adjusted to fit various head sizes, and the ear covering portions are ear pads secured on the outer ends of the headband. In a second embodiment, the headband is a continuous circular configuration formed of flexible elastic material which encircle the person's head and the laterally opposed ear covering portions and pockets are integrally formed on the circular headband. In a third embodiment the article is in the form of a cap having a crown portion which covers the top of the head of the wearer above the ears and is hemmed at its bottom end to form a circular headband portion which covers the ears of the wearer. The packets of exothermic heat dispensing material are activated by exposing them to air, kneading them, or puncturing an inner bag to initiate the heat generating chemical reaction prior to placing them into the pockets.

DESCRIPTION OF THE PREFERRED EMBODIMENT

Figure 1:
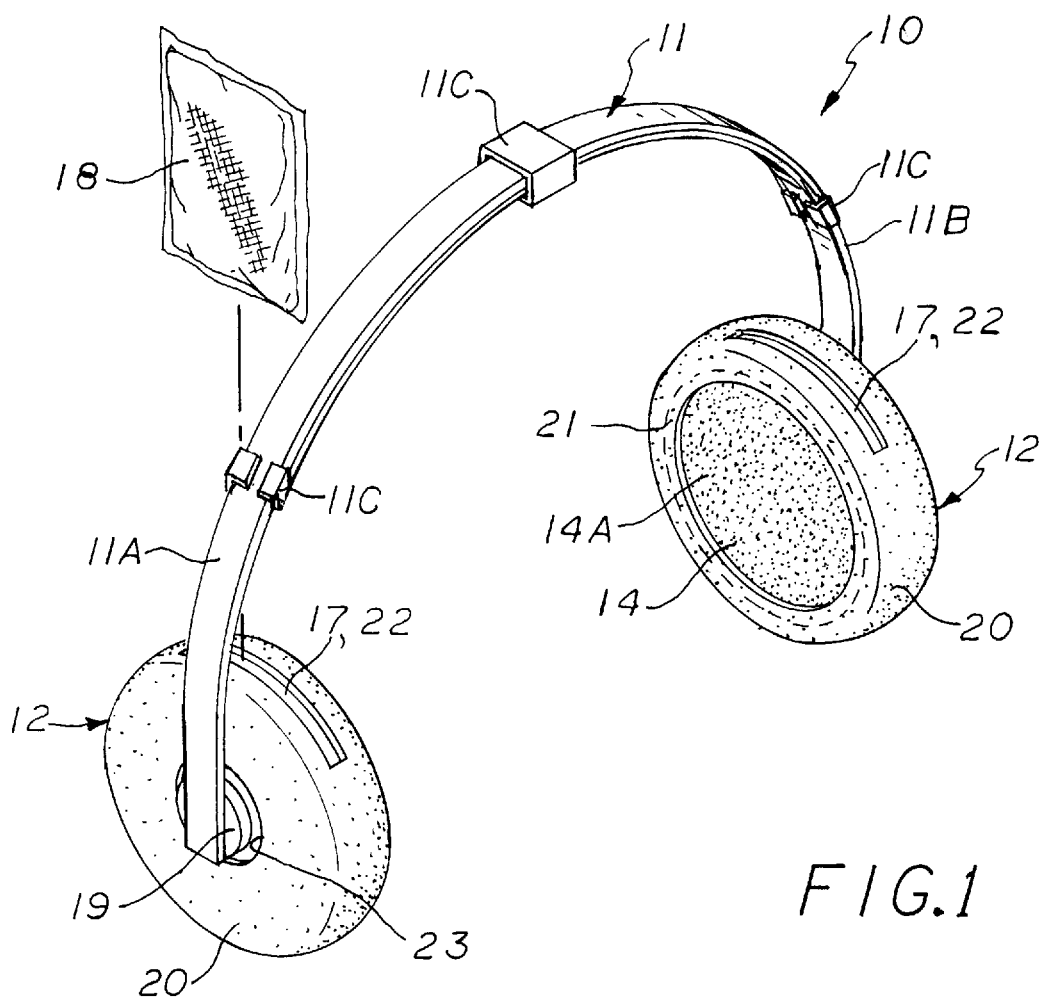
FIG. 1 is a perspective view of an embodiment of the exothermic ear warmer device in accordance with the present invention having a headband with ear pads at each end.
Figure 2:
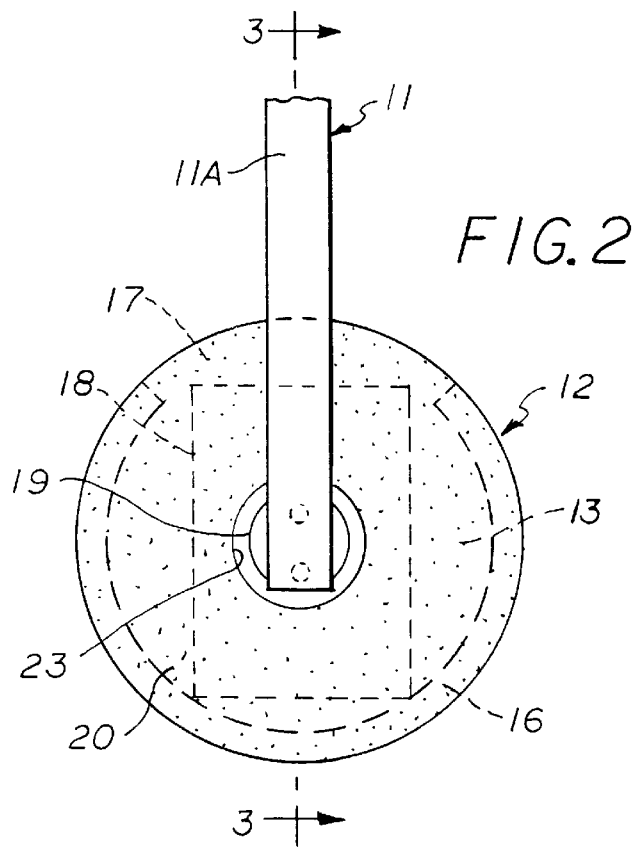
FIG. 2 is a partial side elevation view of the embodiment of FIG. 1.
Figure 3:
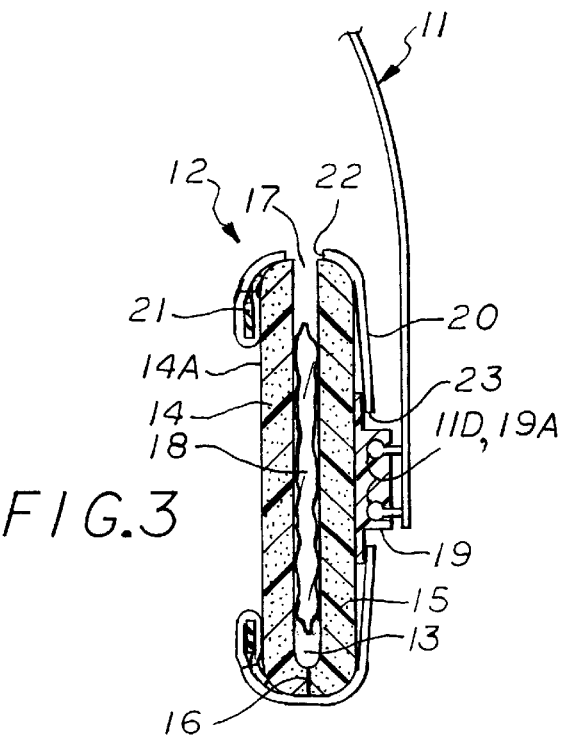
FIG. 3 is a cross section through the ear pad portion of the embodiment of FIG. 1, taken along line 3—3 of FIG. 2.

Referring to the drawings by numerals of reference, there is shown in FIGS. 1, 2, and 3, a first embodiment of preferred ear warming device 10 which includes an adjustable headband 11 having a pair of ear pads 12 secured at each end. The headband 11 is formed of a suitable resilient flexible material, such as plastic or metal, which is which curved to fit over the top of a person's head and biasly engage the ear pads 12 on the outer ears of the wearer. In a preferred embodiment, the headband 11 is formed of a pair of narrow rectangular strips or bands 11A and 11B which are slidably connected in overlapped relation by clamping elements 11C, such that the length of the headband 11 may be adjusted to fit various head sizes.

The ear pads 12 are of generally circular or oval configuration sized and shaped to substantially cover the outer ear of the wearer. Each ear pad 12 has a pocket 13 formed by two layers of material 14 and 15 secured together along peripheral sides, designated as 16, and leaving a portion unsecured to define an opening 17. The pocket 13 is sized to removably receive and enclose a packet of exothermic heat dispensing material 18. The layers of material 14 and 15 within the peripherally secured sides 16 are separable to accommodate the packet 18.

The outer surface 14A of one layer of material 14 is received on the outer ear of the wearer and has a thickness sufficient to prevent burning of the ear when the packet 18 of exothermic heat dispensing material is activated and enclosed in the pocket 13. Preferably, the layer 14 is formed of a suitable porous material, such as a woven fabric or open cell foam rubber or plastic to facilitate thermal permeation therethrough between the ear and the packet of exothermic heat dispensing material 18. The other layer of material 15 may be made of the same material as the layer 14 or made of a different material.

In the illustrated example, the ear pads 12 are connected to the ends of the head band 11 by a releasable connection. The ends of the bands 11A and 11B are provided with a pair of bulbous protrusions 11D. A disk-like connector 19 is secured to the outer surface of the layer 15. The connector 19 has a pair of concave recesses 19A which receive and engage the bulbous protrusions 11D in a snap-fit relation. It should be understood that the ear pads 12 may be connected to the ends of the head band 11 by other means conventional in the art.

The ear pads 12 may also be provided with an outer pouch or covering 20 formed of a soft material shaped to substantially cover the outer layer of material 15. The outer covering 20 may be provided with an elastic band 21 sewn into its periphery so that it can be easily installed and removed from the ear pads 12. The outer covering 20 is also provided with an opening or slot 22 in registry with the opening 17 of the pocket 13, and an opening 23 to accommodate the connection between the pads 12 and the headband 11. Depending upon the type of material used for the outer covering 20, the periphery of the slot 22 may be stitched or hemmed to prevent fraying.

Figure 4:
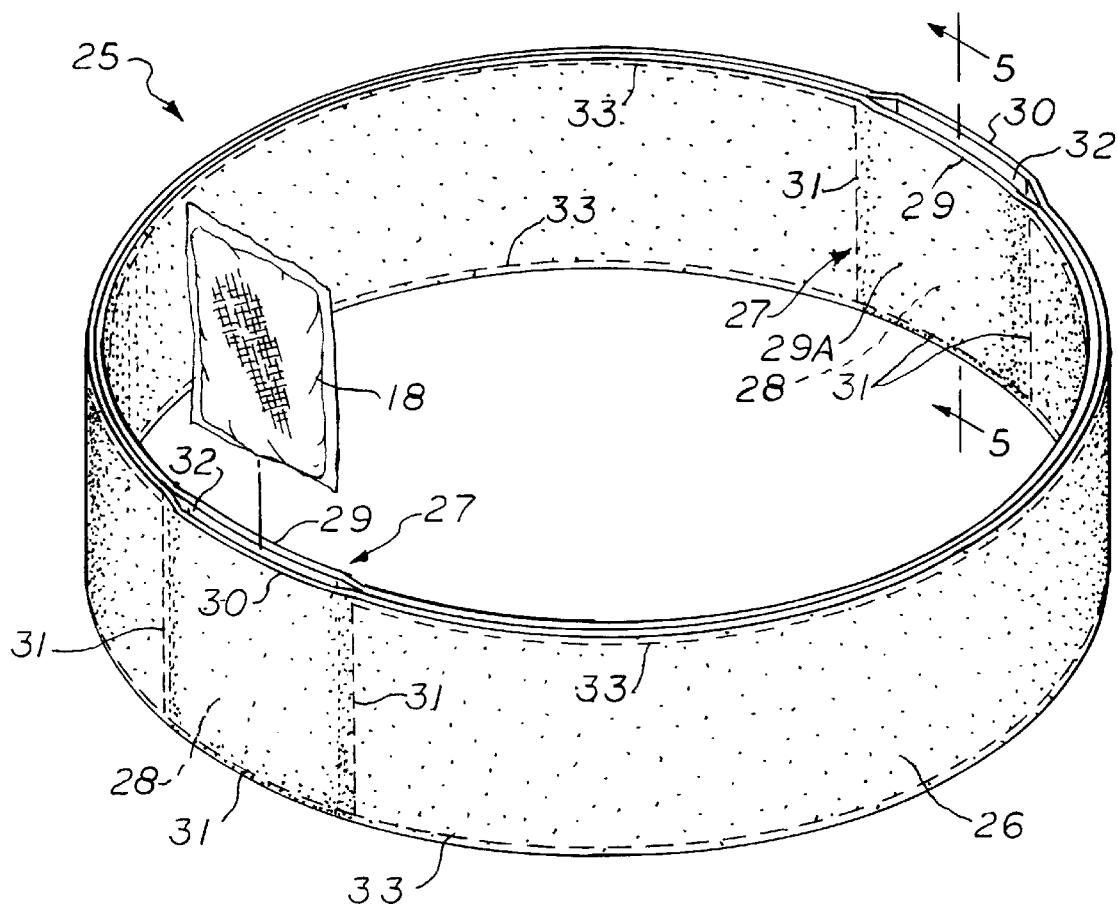
FIG. 4 is a perspective view of another embodiment of the exothermic ear warmer device in accordance with the present invention wherein the headband is a continuous circular configuration and the ear covering portions are integrally formed on the circular headband.
Figure 6:
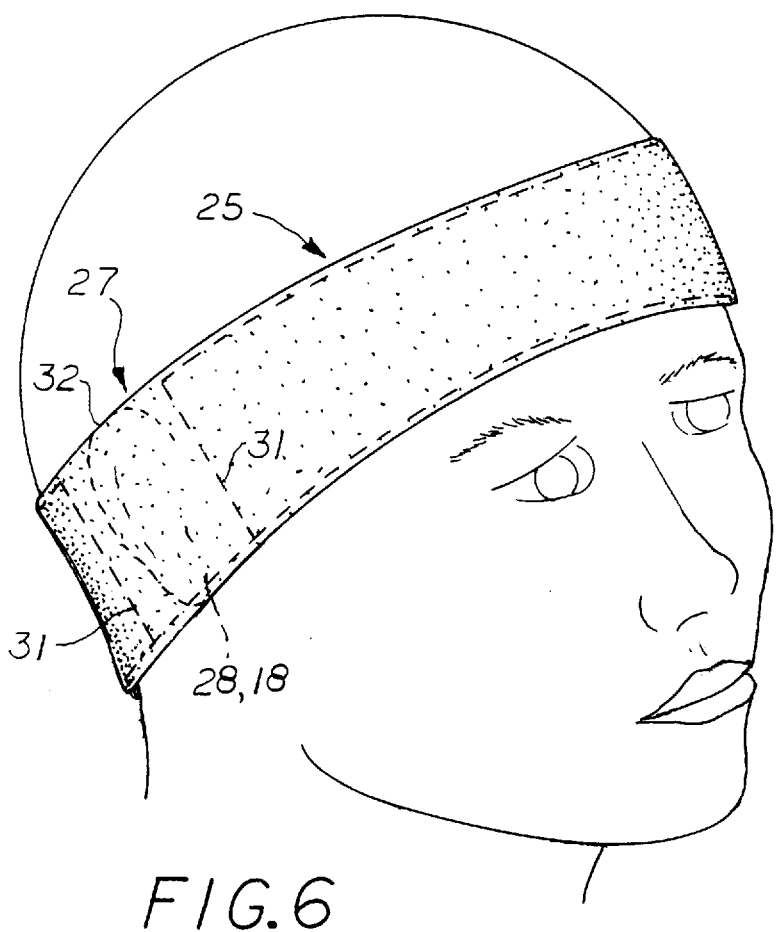
FIG. 6 is a perspective view of the embodiment of FIG. 4 shown on the head of a wearer.
Figure 5:
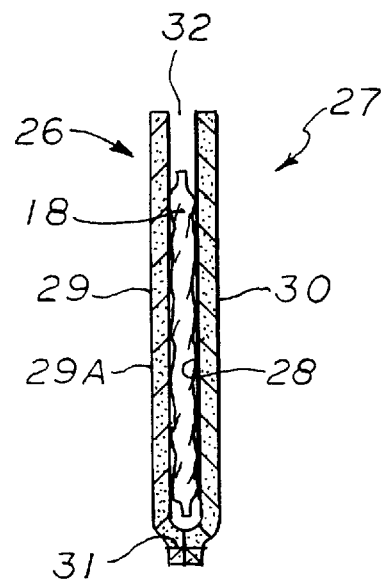
FIG. 5 is a cross section through the ear covering portion of the embodiment of FIG. 4, taken along line 5—5 of FIG. 4.

Referring now to FIGS. 4, 5 and 6, another embodiment of the ear warming device 25 is shown. In this embodiment, the headband 26 is a continuous circular configuration which encircles the head of the wearer and has laterally opposed ear covering portions 27 of sufficient width to substantially cover the ears of the wearer. The headband 26 is formed of a suitable flexible elastic material which, preferably, is porous, such as a woven fabric or open cell foam rubber or plastic material to facilitate thermal permeation.

Each ear covering portion 27 has a pocket 28 formed by two layers of material 29 and 30 secured together along three sides, such as by stitching 31, and leaving one side unsecured to define an opening 32. The pocket 28 has a length and width sufficient to receive and enclose a packet of exothermic heat dispensing material 18. The layers of material 29 and 30 within the peripherally secured sides are separable to accommodate the packet 18. The outer surface 29A of one layer of material 29 is received on the outer ear of the wearer and has a thickness sufficient to prevent burning of the ear when the packet 18 of exothermic heat dispensing material is activated and enclosed in the pocket 28.

The headband 26 may be constructed by sewing a pair of elongate rectangular strips of material together along their longitudinal edges, such as by stitching 33, leaving a portion unsecured at two places to define the pocket openings 32, sewing the two strips of material together by vertical stitching 31 at parallel spaced locations to define the pockets 28, and then sewing the ends of the elongate rectangular strips of material together to form the continuous circular configuration 26. In this method, the entire headband 26 would have the two layers 29 and 30.

The headband 26 may also be constructed by sewing a pair of single layer short rectangular strips of material along three sides onto an elongate single layer rectangular strip of material to form the pockets 28 and the securing the ends of the single layer elongate rectangular strip together to form the continuous circular configuration 26. In this method, only the ear covering portions 27 would have the two layers 29 and 30.

Depending upon the material used for the headband 26 the periphery of the pocket openings 32 may be stitched or hemmed to prevent fraying.

Figure 7:
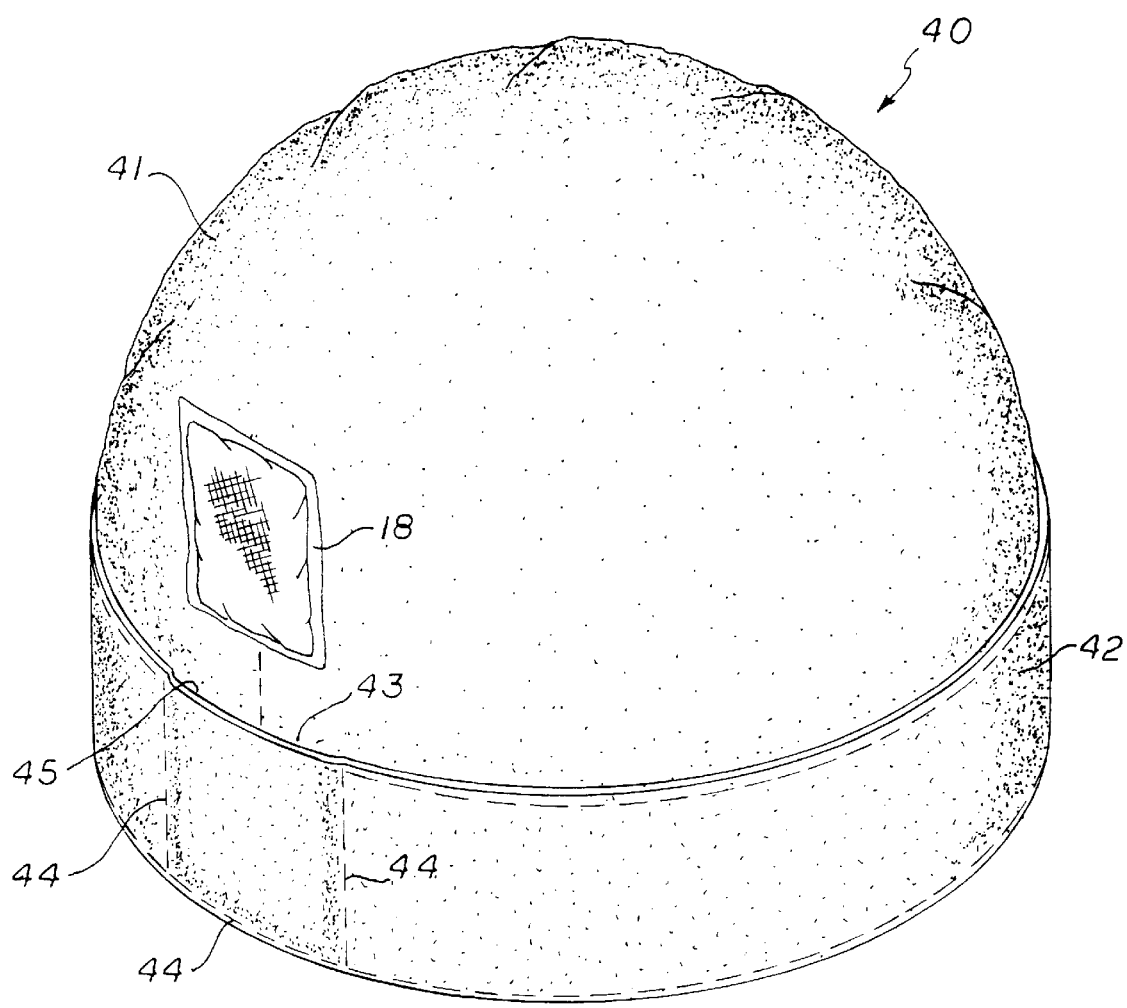
FIG. 7 is a perspective view of another embodiment of the exothermic ear warming device in the form of a cap having a crown portion to cover the top of the head of the wearer above the ears and is hemmed at its bottom end to form an integral headband portion which encircles the head of the wearer and covers the ears of the wearer.

FIG. 7 shows another embodiment of the ear warming device in the form of a cap 40 having a crown portion 41 which is shaped to cover the top of the head of the wearer above the ears and is hemmed at its bottom end to form an integral continuous circular headband portion 42 which encircles the head of the wearer and is of sufficient width to substantially cover the ears of the wearer. The cap 40 is formed of a suitable flexible elastic fabric which, preferably, is porous, such as a woven fabric to facilitate thermal permeation.

The headband portion 42 has laterally opposed pockets 43 formed by securing the overlapped layers of the material together along three sides, such as by stitching 44, and leaving the top side unsecured to define an opening 45. Each pocket 43 has a length and width sufficient to receive and enclose a packet of exothermic heat dispensing material 18. The layers of material within the peripherally secured sides are separable to accommodate the packet 18.

Various commercially available exothermic heat dispensing packets 18 may be used in the embodiments of the present invention, such as those which require exposure to air, kneading, or puncturing of an inner bag to mix the chemical and start the heat generating reaction. The preferred exothermic heat dispensing packet 18 is activated by exposure to air.

U.S. Pat. No. 3,976,049, incorporated herein by reference, discloses an air activated exothermic hand warmer packet marketed by "Grabber" (tm) of concord, CA under the tradename "Grabber Mycoal" would be suitable for use in the present invention. This particular warmer and air tight envelope utilizes a mixture of iron powder, water, cellulose, vermiculite activated carbon, and salt, enclosed in a laminated bag having an air permeable cloth layer and an impermeable film layer containing aeration holes. After exposure to the air, the warmer produces heat in the temperature range of from about 104° F. to about 156° F. which is generated by the oxidation of the iron powder and may last for about 7 hours or more. It should be understood that various other types of exothermic heat dispensing packets may also be used.

To install the exothermic heat dispensing packets 18, the wearer simply removes the exothermic heat dispensing packets from their sealed package and depending upon the type used, exposes them to the air, kneads them, or punctures the inner bag to initiate the heat generating chemical reaction, and then places them into the pockets 13, 28, or 43.

While this invention has been described fully and completely with special emphasis upon preferred embodiments, it should be understood that within the scope of the appended claims the invention may be practiced otherwise than as specifically described herein.

I claim:

1. An ear covering headgear article for containing exothermic heating elements to warm the ears of a wearer comprising:

an article of headgear having a headband portion formed of at least one band of resilient flexible material curved to fit over the top of a person's head and having a pair of laterally opposed ear pads of generally circular configuration, each secured on an outer end of said at least one band of resilient flexible material and sized and shaped to substantially cover the ears of a wearer; and a pocket in each of said ear pads formed by two layers of material each having a periphery, said two layers of material secured together along peripheral sides with an upper portion of said peripheries of said two layers being left unsecured to define an opening and an interior sized to removably receive and enclose a packet of exothermic heat dispensing material.

2. The headgear article according to claim 1 wherein one of said layers of material of each said pocket has an outer surface to be received on the outer ear of a wearer and has a thickness sufficient to prevent burning of the ear when said packet of exothermic heat dispensing material is activated and enclosed in said pocket.

3. The headgear article according to claim 1 wherein one of said layers of material of each said pocket is sufficiently porous to facilitate thermal permeation and has an outer surface to be received on the outer ear of a wearer and has a thickness sufficient to prevent burning of the ear when said packet of exothermic heat dispensing material is activated and enclosed in said pocket.

4. The headgear article according to claim 1 wherein said headband portion is formed of two curved bands of resilient flexible material slidably connected in overlapped relation such that the length of the headband portion may be adjusted to fit various head sizes.

5. The headgear article according to claim 1 further comprising an outer covering formed of soft material on each said ear pad, and each outer covering having a slot in registry with said pocket opening.

6. The headgear article according to claim 1 further comprising a packet of exothermic heat dispensing material removably received and carried in each said pocket.

7. The device according to claim 1 further comprising an outer covering formed of soft material on each said ear pad, and each outer covering having a slot in registry with said pocket opening.

8. An exothermic ear warmer device worn on the head of a person to warm the ears of a wearer comprising:

a headband formed of at least one band of resilient flexible material curved to fit over the top of a person's head and having a pair of laterally opposed ear pads of generally circular configuration, each secured on an outer end of said at least one band of resilient flexible material and sized and shaped to substantially cover the ears of a wearer;

a pocket in each of said ear pads formed by two layers of material each having a periphery, said two layers of material secured together along peripheral sides with an upper portion of said peripheries of said two layers being left unsecured to define an opening and an interior sized to removably receive and enclose a packet of exothermic heat dispensing material; and a packet of exothermic heat dispensing material removably received and carried in each said pocket.

9. The device according to claim 8 wherein one of said layers of material of each said pocket has an outer surface to be received on the outer ear of a wearer and has a thickness sufficient to prevent burning of the ear when said packet of exothermic heat dispensing material is activated and carried in said pocket.

10. The device according to claim 8 wherein one of said layers of material of each said pocket is sufficiently porous to facilitate thermal permeation and has an outer surface to be received on the outer ear of a wearer and has a thickness sufficient to prevent burning of the ear when said packet of exothermic heat dispensing material is activated and enclosed in said pocket.

* * * * *